US00PP37329P2

(12) United States Plant Patent
Slaughter et al.

(10) Patent No.: US PP37,329 P2
(45) Date of Patent: Mar. 17, 2026

(54) PEACH TREE NAMED 'THREEFOLDPEACHONE'

(50) Latin Name: *Prunus persica*
Varietal Denomination: Threefoldpeachone

(71) Applicant: Threefold Holdings Group, LLC, Reedley, CA (US)

(72) Inventors: John K. Slaughter, Fresno, CA (US); Kaylan M. Roberts, Fresno, CA (US)

(73) Assignee: Threefold Holdings Group, LLC, Reedley, CA (US)

( * ) Notice: Subject to any disclaimer, the term of this patent is extended or adjusted under 35 U.S.C. 154(b) by 0 days.

(21) Appl. No.: 19/183,660

(22) Filed: Apr. 18, 2025

(51) Int. Cl.
*A01H 5/08* (2018.01)

(52) U.S. Cl.
USPC ..... Plt./197

(58) Field of Classification Search
USPC ..... Plt./197
CPC ..... A01H 6/7463; A01H 5/08
See application file for complete search history.

*Primary Examiner* — Keith O. Robinson
(74) *Attorney, Agent, or Firm* — Michelle Bos Legal LLC

(57) ABSTRACT

A new and distinct peach tree (*Prunus persica*) named 'Threefoldpeachone', which produces an attractively colored yellow-fleshed, non-melting, clingstone peach that is mature for harvesting and shipment approximately June 2 to June 10 under the ecological conditions prevailing in the San Joaquin Valley of central California.

1 Drawing Sheet

Botanical designation: '*Prunus persica*'.
Varietal denomination: 'Threefoldpeachone'.

BACKGROUND OF THE NEW VARIETY

The present variety of peach tree resulted from a program of fruit tree breeding. The purpose of this program is to improve the commercial quality of deciduous fruit varieties and rootstocks by creating and releasing promising selections of *Prunus* species. To this end, both controlled and hybrid cross pollinations are made each year to produce seedling populations from which improved progenies are evaluated and selected.

The 'Threefoldpeachone' peach tree originated in a population of seedlings growing in experimental orchard located near Fresno, California. The breeders pollinated an unnamed, unpatented female parent (peach, *Prunus persica*) with an unnamed, unpatented male parent (nectarine, *Prunus persica* var. *nucipersica*). In 2010, seeds obtained from the resulting fruit were planted in pots and grown in a greenhouse as seedlings. The seedlings were later field-planted on their own roots for further growth and observation. The peach tree described and claimed herein was among those seedlings, and was of interest to the breeders because it exhibited desirable characteristics. The seedline, assigned breeder reference 'H5.003' and later designated 'Threefoldpeachone', was marked for further observation. After the 2013 fruiting season, the new peach tree was selected for advanced evaluation and repropagation.

ASEXUAL REPRODUCTION

The first asexual reproduction of the 'Threefoldpeachone' took place near Fowler, California in 2013, by budding onto 'Nemaguard' rootstock (not patented). The claimed plant has been observed to remain true-to-type over successive asexually propagated generations. The distinguishing characteristics of the original tree and its fruit are well-established and appear to be uniformly transmitted through succeeding asexual propagations.

SUMMARY OF VARIETY

'Threefoldpeachone' is a new and distinct peach tree of relatively large size and vigorous growth. The new tree is a regular and productive bearer of relatively large, firm, yellow-fleshed, non-melting clingstone fruit having desirable flavor, flesh texture and eating qualities.

The claimed peach tree has a medium-low chilling requirement of approximately 250 hours, and produces relatively uniformly-sized fruit throughout the canopy. 'Threefoldpeachone' peaches are typically ripe for commercial harvesting and shipment from about June 2 to about June 10 under the ecological conditions prevailing in the San Joaquin Valley of central California. The fruit exhibits good handling and shipping qualities.

The claimed plant is distinguished from its unnamed, unpatented female parent by its fruit, which exhibits non-melting flesh as compared to the melting flesh of the female parent. Additionally, fruit from the claimed plant achieves significantly more external red blush coloration as compared to the female parent. The distinguishing difference between the claimed peach tree and its male parent is that the male parent is a nectarine tree. In comparison to 'June Time' (U.S. Plant Pat. No. 23,530), the closest known yellow-fleshed peach variety, 'Threefoldpeachone' ripens 7 to 9 days earlier and expresses 2% to 3% higher soluble solids as compared to fruit from the 'June Time' peach tree.

BRIEF DESCRIPTION OF THE DRAWINGS

The attached photographs were taken near Fresno, California in 2016. The colors are as true as is reasonably possible in a color representation of this type, but are subject to variation due to differences in printing methods and electronic displays. Accordingly, reference should be made to the color descriptions provided in the detailed description of the variety below.

NOT A COMMERCIAL WARRANTY

Figure 1:
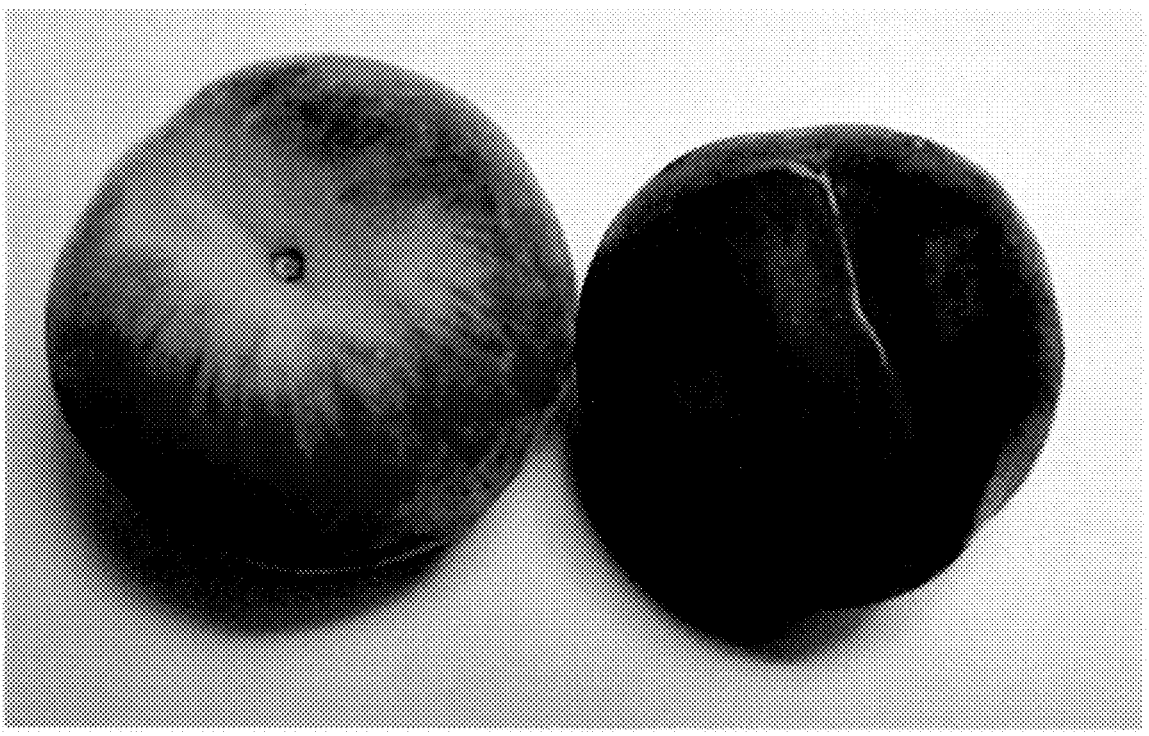
FIG. 1 is a color photograph of two whole mature fruits of the claimed variety, harvested from a 12th leaf tree.
Figure 2:
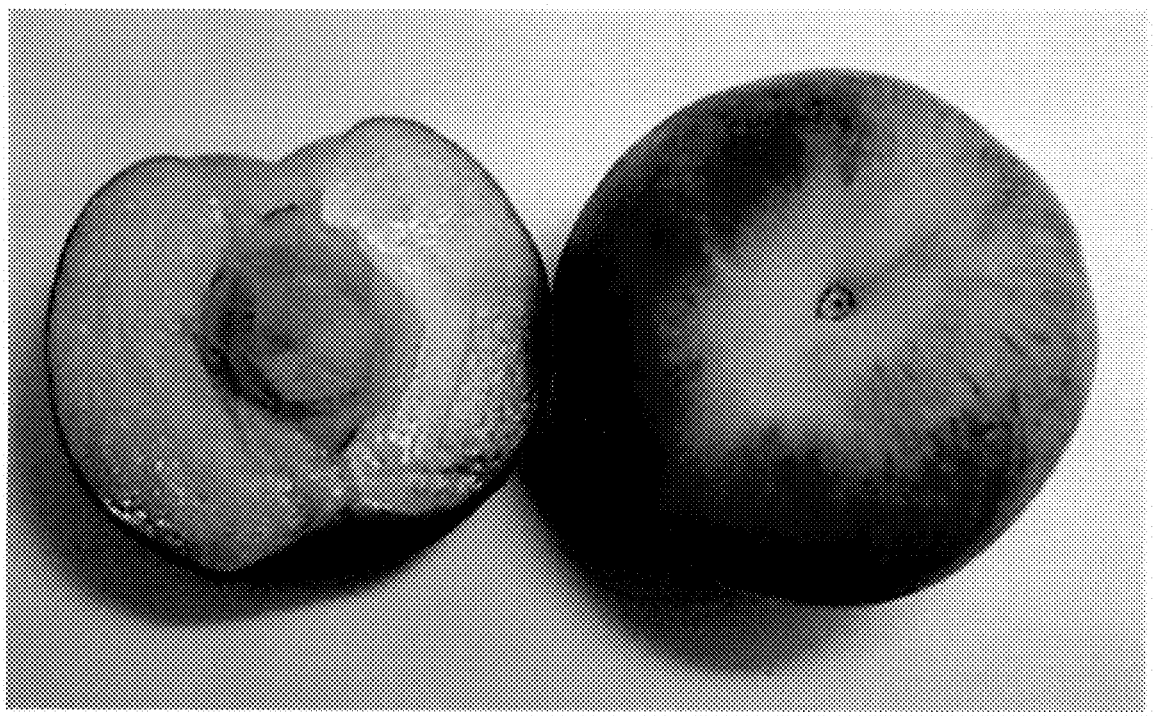
FIG. 2 is a color photograph of a whole and sectioned matured fruit of the claimed variety.

The following detailed description has been prepared to solely comply with the provisions of 35 U.S.C. § 112 and does not constitute a commercial warranty (either expressed or implied) that the present variety will in the future display all the botanical, pomological, or other characteristics as set forth hereinafter. Therefore, this disclosure may not be relied upon to support any future legal claims including, but not limited to, breach of warranty of merchantability or fitness for any purpose, or non-infringement which is directed, in whole, or in part, to the present variety.

DETAILED DESCRIPTION

Referring more specifically to the details of this new and distinct variety of peach tree, the following has been observed during the sixth fruiting season on multiple replicated trees and under the ecological conditions prevailing at orchards located near Fresno, California. The described trees were grown on 'Nemaguard' rootstock (not patented). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average. All colors are described with reference to The R.H.S. Colour Chart, $4^{th}$ ed. (Royal Horticultural Society 2001).

Tree:

*Size*.—The tree of the present variety was pruned to a height of about 290.0 cm to about 320.0 cm at commercial maturity.

*Width*.—About 305.0 cm.

*Vigor*.—Very vigorous as compared to other common commercial peach cultivars ripening in the early season of maturity. The present peach tree variety grew from about 195.0 cm to about 200.0 cm in height during the first growing season. The new variety was pruned to a height of about 170.0 cm after the first dormant season, and primary scaffolds were then selected for the desired tree structure.

*Productivity*.—Productive. Fruit set varies, from more than the desired crop load to levels higher than desired amounts when the new variety is grown in a suitable horticultural zone and under appropriate commercial nursery conditions. The fruit set is spaced by thinning to develop the remaining fruit into the desired market- sized fruit. The quantity of fruit set varies with the prevailing climatic conditions and the cultural practices employed.

*Fruit bearing*.—Regular. Fruit set has been adequate during the previous years of observation, and thinning was necessary during the past 10 years on both the original seedling and on subsequent asexually reproduced trees.

*Tree form*.—Upright and pruned into a vase shape.

*Density*.—Moderate.

*Hardiness*.—The present tree was grown and evaluated in USDA Hardiness Zone 9. The calculated winter chilling requirement of the new tree is approximately 250 hours at a temperature below 7.0 degrees C. Hardy under typical central San Joaquin Valley climatic conditions.

Trunk:

*Diameter*.—About 26.0 cm in diameter when measured at about 15.5 cm above the soil level. This measurement was taken from replicated trees at the beginning of the tenth growing season.

*Bark texture*.—Moderately rough with an abundance of lenticels.

*Lenticels*.—Numerous flat, oval lenticels are present. The lenticels range in size from about 5.0 mm to about 8.0 mm in width, and between about 2.0 mm and about 3.0 mm in height. Density is approximately 6 per square cm.

*Lenticel color*.—Orange brown (RHS Greyed-Orange Group 167B).

*Bark coloration*.—Variable, generally greyed tan (RHS Grey-Brown Group N199D).

Branches:

*Size*.—Medium-large; length varies due to pruning, generally about 140 cm to 155.0 cm.

*Diameter*.—Average as compared to other peach varieties. The branches have a diameter of about 16.0 cm when measured during the tenth year after grafting.

*Flowering shoot thickness*.—Average for the species. Generally, the most consistent flower bud development and, therefore, potential fruiting sites occur on annual shoots which are about 7.5 mm to 10 mm in diameter or larger, but generally less than about 10.0 millimeters in diameter at the time of bloom.

*Surface texture*.—Average and appearing relatively smooth.

*Crotch angles*.—Variable on primary branches; usually growing at an angle of about 50 degrees when measured from a horizontal plane.

*Current season shoots*.—Surface texture — Substantially glabrous.

*Internode length*.—About 2.2 cm to about 2.8 cm.

*Mature branch color*.—Approximately Grey brown (RHS Greyed-Brown Group N199D).

*Current season shoot color*.—Light green (RHS Yellow-Green Group N144A) with light green (RHS Yellow-Green Group N144C) tips.

Leaves:

*Size*.—Relatively large for the species. Leaf measurements have been taken from vigorous, upright, current-season growth, at approximately mid-shoot.

*Leaf length*.—About 170.0 mm to about 178.0 mm including the petiole.

*Leaf width*.—About 32.0 mm to about 37.0 mm.

*Leaf base shape*.—The leaves generally exhibit equal marginal symmetry relative to the leaf longitudinal axis.

*Leaf form*.—Lanceolate.

*Leaf tip form*.—Acuminate.

*Leaf color*.—Upper Leaf Surface — Medium green (approximately RHS Green Group 137B).

*Leaf texture*.—Upper Leaf Surface — Glabrous; Lower Leaf Surface — Glabrous.

*Leaf color*.—Lower Leaf Surface — Medium green (approximately RHS Green Group 137D).

*Leaf venation*.—Pinnately veined.

*Mid-vein*.—Color — Light yellow (approximately RHS Greyed-Yellow Group 160C).

*Leaf margins*.—Gently undulating. Form — Considered crenate. Uniformity — Generally uniform.

*Leaf petioles*.—Form — Canaliculated. Relative size — Medium for the species. Length — About 8.0 mm to 10.0 mm Diameter — About 1.7 mm to about 2.1 mm. Color — Light yellow-green (approximately RHS Yellow-Green Group 144B).

*Texture*.—Glabrous.

*Strength*.—Durable for species until senescence.

*Leaf glands*.—Size — Relatively small for the species; about 1.0 mm in width; and about 1.5 mm in height. Number — Generally one per marginal side. Occasionally, two glands per side are found. Observations of more than two glands per marginal side are very uncommon. Type — Glands located at the axis of the leaf base and the petiole are globose in shape. Color — Considered a pale olive green (approximately RHS Greyed-Green Group 148C).

*Leaf stipules*.—Relative size — Medium for this species, approximately 8.0 mm to 16.0 mm long and 1.0 mm to 2 mm wide. Quantity — Typically, 2 per leaf bud and up to 6 per shoot tip. Form — Lanceolate in form and having a serrated marginal edge. Color — Green (approximately RHS Green Group 143C).

Flower buds:

*Hardiness*.—No winter injury (bud death) has been noted during the last several years of observation in the central San Joaquin Valley. The new peach tree has not been intentionally subjected to extremes of drought, cold or heat stress, and therefore this information is not available.

*Flower bud*.—Size — Variable and dependent on the state of maturity. The flower buds described were observed approximately 7 days prior to bloom.

*Length*.—About 11.5 mm.

*Diameter*.—About 7.0 mm.

*Surface texture*.—Pubescent.

*Orientation*.—Considered appressed.

*Bud scale color*.—Approximately RHS Greyed-Red Group 178B.

Flowers:

*Date of first bloom*.—Observed on Feb. 10, 2023.

*Blooming time*.—Considered average to early bloom in relative comparison to other commercial peach cultivars grown in the central San Joaquin Valley. The date of full bloom was observed on Feb. 17, 2023. The date of full bloom varies slightly with climatic conditions and prevailing cultural practices.

*Duration of bloom*.—Approximately 8 or more days. This characteristic varies slightly with the prevailing climatic conditions.

*Flower class*.—Perfect; complete and perigynous.

*Flower type*.—Showy.

*Flower size*.—Medium for the species. Diameter at full bloom is about 44.0 mm to about 46.0 mm.

*Bloom quantity*.—Abundant.

*Flower bud density*.—Moderately dense.

*Flower bud frequency*.—Generally, two flower buds per node. Occasionally, one flower bud per node is observed. Very rarely, three floral buds per node are observed.

*Relative petal size*.—Medium for this species.

*Petal length*.—About 17.0 mm to about 20.0 mm.

*Petal width*.—Narrow, about 10.0 mm to 12.0 mm.

*Petal form*.—Oblanceolate.

*Petal count*.—Nearly always 5.

*Petal texture*.—Upper Petal Texture — Very finely pubescent, satin-like. Lower Petal Texture — Very finely pubescent, satin-like.

*Petal color*.—Pink (RHS Red-Purple Group 62B) at popcorn stage.

*Fragrance*.—Slight, sweet; typical of *Prunus persica* species.

*Petal claw*.—Form — Ovate, relatively small. Length — About 9.0 mm. Width — About 7.0 mm.

*Petal margins*.—Slightly undulate.

*Petal apex*.—Exhibits no notch at the apex.

*Flower pedicel*.—Length — Medium, about 6.0 mm to about 8.0 mm. Diameter — About 2.0 mm. Color — Pale brown (approximately RHS Grey-Brown Group 199A). Strength — Tenacious. Average for the species. Texture — Generally smooth.

*Floral nectaries*.—Color — Very pale yellow (approximately RHS Yellow-Orange Group 18 B).

*Calyx*.—Surface Texture — Generally glabrous. Color — Brownish purple. (approximately RHS Greyed-Orange Group 176A).

*Sepals*.—Upper Surface Texture — Moderately pubescent. Lower Surface Texture — Finely pubescent. Quantity — 5 sepals. Relative Size — Medium. Sepal Length — About 6.0 mm to about 7.0 mm. Sepal Width — About 5.0 mm to about 6.0 mm. Sepal Shape — Generally obovate. Sepal Margin — Smooth, entire. Sepal Color — Approximately RHS Greyed-Purple Group N187D.

*Anthers*.—Size — Average for species Color — Yellow when viewed dorsally and just prior to dehiscence (approximately RHS Yellow Group 92C). Position Relative to Stigma — Generally, the stigma is superior to the anthers by about 1.0 mm.

*Pollen production*.—Pollen is abundant and has a yellow color (approximately RHS Yellow-Orange Group 17D).

*Fertility*.—Self-fertile.

*Filaments*.—Size — About 13.0 mm to about 15.0 mm in length. Color — White to pinkish-white (RHS White Group N155D).

*Pistil*.—Quantity — Usually one, and only rarely more than one. Relative Size — Medium. Length — About 16.0 mm to about 19.0 mm in length including the ovary. Color — Very yellow white (approximately RHS Greyed-Yellow Group 160 D). Surface Texture — Pubescent. Ovary Texture — Pubescent. Position Relative to Petals — At flower maturity the pistils grow to be about 3.0 mm superior to the petals.

*Shape*.—The stigma of the pistil is wider than the general diameter of pistil.

Fruit:

*Maturity when described*.—Firm ripe condition (shipping ripe).

*Date of first picking*.—Approximately Jun. 2, 2024.

*Date of last picking*.—Early mid-season Approximately Jun. 10, 2024.

*Size*.—Generally — Medium-large for early mid-season varieties.

*Average cheek diameter*.—About 75.0 mm to about 83.0 mm.

*Average axial diameter*.—About 78.0 mm to about 85.0 mm.

*Typical weight*.—About 180.0 grams.

*Fruit soluble solids*.—About 13.5 to about 15.6 Brix.

*Fruit firmness*.—Fruit flesh pressures averaged 14.0 pounds at the time the fruit was analyzed.

*Titratable acidity*.—About 0.68 percent at commercial harvest maturity.

*Fruit form*.—Globose, symmetrical.

*Mucron tip*.—Rarely observed.

*Fruit suture*.—No stitching exists along the suture line.

*Suture*.—Color — Generally, the fruit appears blushed to the same degree as the skin (approximately RHS Orange-Red Group N34A).

*Ventral surface*.—Form-Even, uniform in appearance when viewed from the lateral, sutural plane.

*Apex shape*.—Indented with a retuse tip.

*Base shape*.—Flat to weakly depressed.

*Stem cavity*.—Shape — Rounded, narrow oval form, generally uniform; slightly extended toward the suture. Depth — About 6.0 mm to about 8.0 mm. Width — About 15.0 mm. Length — About 45.0 when measured in the sutural plane.

*Fruit skin*.—Thickness — Medium, tenacious to the flesh. Surface Texture — Pubescent. Taste — Sweet with balanced acid/sugar ratio. Tendency to crack — Not observed to date.

*Fruit skin color*.—Blush Color — Deep red blush over much of the skin (approximately RHS Greyed-Purple Group 187B), more typically present on the portions of the fruit facing the sunlight. The blush covers about 75% to about 90% of the fruit skin surface. Ground Color — Medium yellow (approximately RHS Yellow Group 4A).

*Fruit glossiness*.—Not glossy.

*Pubescence*.—Mild; medium density.

*Fruit stem*.—Relative Size — Medium. Length — About 7.5 mm to about 9.5 mm. Diameter — About 2.0 mm to about 3.0 mm. Color — Pale yellow green (approximately RHS Yellow-Green Group N144D).

*Fruit flesh*.—Ripening — Ripens evenly, generally from the apex to the basal end. Texture — Firm, juicy, and dense; Non-melting. Fibers — Present but not prominent. Aroma — Present, typical of peaches. Eating Quality — Good. Flavor — Balanced with sweetness and slight acidity. Juice Production — Moderate. Brix — About 13.5 degrees to about 15.6 degrees. Acidity — Considered medium. Approximately 0.68 percent titratable acidity at fruit harvest. Flesh Color — Medium yellow (approximately RHS Yellow Group 13C) with some pale greenish yellow nearer the stem end (RHS Yellow Group 145C). With increasing maturity red (approximately RHS Red Group 45B) coloration can be observed internally from the periphery of the flesh, creating a halo appearance.

Stone:

*Type*.—Clingstone.

*Size*.—Medium for the species. Length — Average, about 22.0 mm to about 26.0 mm. Width — Average, about 18.0 mm to about 22.0 mm. Diameter — Average, about 17.0 mm to about 18.5 mm.

*Form*.—Obovate. Base Shape — Equilateral. Apex Shape — Acute.

*Stone surface*.—Texture — Furrowed. Ridges — Present in a longitudinal pattern. Ventral Edge — Smooth, not protruding. Dorsal Edge — Smooth, not protruding.

*Stone color*.—Mature, dry stone is pale brown (approximately RHS Greyed-Orange Group 164C).

*Tendency to split*.—Splitting has rarely been noted.

*Kernel*.—Relative Size — Medium for species. Length — About 12.0 mm to about 19.0 mm. Width — About 12.0 mm to about 17.0 mm. Thickness — About 4.0 mm to about 5.0 mm. Form — Ovoid. Kernel Surface Texture — Pellicle shortly pubescent. Color — Dark tan (RHS Greyed-Orange Group 164B).

*Use*.—Early mid-season maturating fruit is firm and attractively colored, useful for local, long-distance and export shipping.

*Keeping quality*.—Excellent. Fruit has been observed to store well for periods of up to 25 days after harvest at 1.0 degree Celsius.

*Shipping quality*.—Good. Fruit shows minimal bruising of flesh or damage to skin after being subjected to normal harvesting and packing procedures.

*Resistance to insects and disease*.—No susceptibilities were noted. The present variety has not been intentionally tested to expose or detect any susceptibilities or resistances to any known plant or fruit diseases, insects, frost, winter injury, or other environmental factors.

Although the 'Threefoldpeachone' peach tree possesses the described characteristics when grown under the ecological conditions prevailing near Fowler, California, in the Central part of the San Joaquin Valley of California, variations of the usual magnitude and characteristics incident to changes in growing conditions, fertilization, nutrition, pruning, pest control, frost, climatic variables, and changes in horticultural management are to be expected.

What is claimed is:

1. A new and distinct peach tree named 'Threefoldpeachone' substantially as illustrated and described, characterized principally as to novelty by producing an attractively colored yellow-fleshed, non-melting, clingstone peach which is mature for harvesting and shipment approximately June 2 to June 10 under the ecological conditions prevailing in the San Joaquin Valley of central California.

* * * * *